United States Patent [19]

Stuart et al.

[11] Patent Number: 5,114,401
[45] Date of Patent: May 19, 1992

[54] METHOD FOR CENTRAL VENOUS CATHETERIZATION

[75] Inventors: Regina K. Stuart, Brighton; Jeffrey A. Lowell, Dorchester; John K. Baxter, III, Belmont; Bruce R. Bistrian, Ipswich; Scott Shikora, Brighton, all of Mass.

[73] Assignee: New England Deaconess Hospital Corporation, Boston, Mass.

[21] Appl. No.: 483,906

[22] Filed: Feb. 23, 1990

[51] Int. Cl.$^5$ .............................................. A61M 31/00
[52] U.S. Cl. ...................... 604/53; 604/161; 604/117
[58] Field of Search ............... 604/117, 158–170, 604/49, 51–53, 95, 282; 128/772

[56] References Cited

U.S. PATENT DOCUMENTS

| | | | |
|---|---|---|---|
| 3,605,750 | 9/1971 | Sheridan et al. | 604/280 |
| 4,327,722 | 5/1982 | Groshong et al. | 128/214.4 |
| 4,525,157 | 6/1985 | Vaillancourt | 604/52 |
| 4,553,960 | 11/1985 | Lazarus et al. | 604/158 |
| 4,645,491 | 2/1987 | Evans | 604/158 |
| 4,650,472 | 3/1987 | Bates | 604/158 |
| 4,652,256 | 3/1987 | Vaillancourt | 604/52 |
| 4,655,750 | 4/1987 | Vaillancourt | 604/165 |
| 4,687,469 | 8/1987 | Osypka | 604/161 |
| 4,690,138 | 9/1987 | Heyden | 128/207.15 |
| 4,710,171 | 12/1987 | Rosenberg | 604/117 |
| 4,733,661 | 3/1988 | Palestrant | 128/303 B |
| 4,737,146 | 4/1988 | Amaki et al. | 604/51 |
| 4,748,982 | 6/1988 | Horzewski et al. | 128/344 |
| 4,753,637 | 6/1988 | Horneffer | 604/53 |
| 4,760,847 | 8/1988 | Vaillancourt | 128/329 R |
| 4,772,649 | 9/1988 | Cragg | 604/158 |
| 4,798,193 | 1/1989 | Giesy et al. | 128/7 |
| 4,813,930 | 3/1989 | Elliott | 604/53 |
| 4,900,314 | 2/1990 | Quackenbush | 604/282 |
| 4,951,686 | 8/1990 | Herlitze | 128/772 |
| 4,969,875 | 11/1990 | Ichikawa | 604/164 |

Primary Examiner—John D. Yasko
Assistant Examiner—Adam J. Cermak

[57] ABSTRACT

Disclosed are an apparatus and methods for initial, or replacement, central venous catherization using a flexible guidewire with markings thereon and a substantially translucent non-thrombogenic catheter. In operation, the guidewire is inserted along a catheter positioned in a vein. The marks on the guidewire are then used to establish, and maintain as constant, the position of the guidewire. Next, the catheter already in the vein is removed by sliding it over the guidewire, and a new catheter is slipped over the guidewire into position. Once the new catheter is positioned, the guidewire is removed.

15 Claims, 3 Drawing Sheets

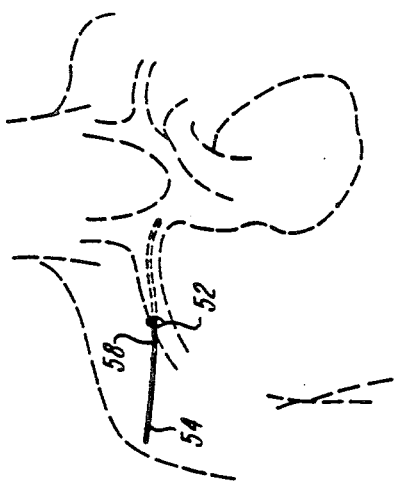
FIG. 4A
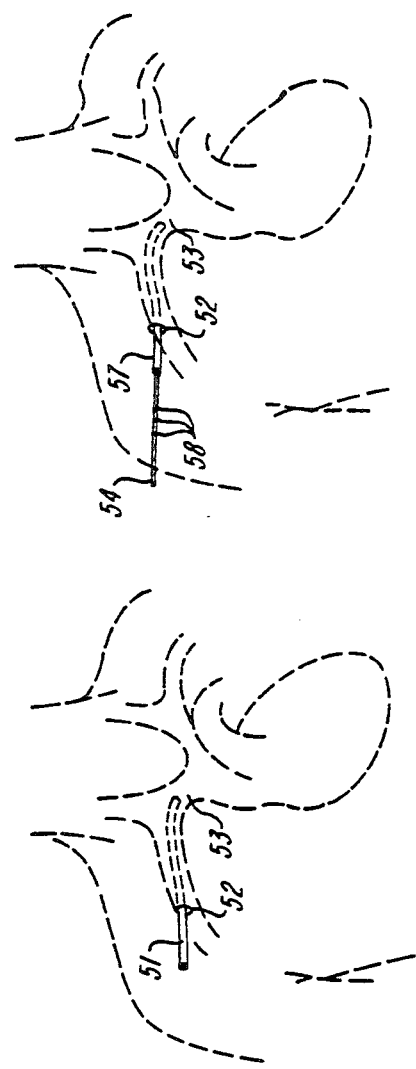
FIG. 4B
FIG. 4C
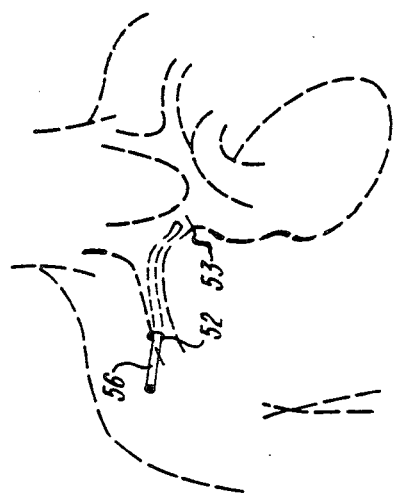
FIG. 4D
FIG. 4E

METHOD FOR CENTRAL VENOUS CATHETERIZATION

BACKGROUND OF THE INVENTION

This invention relates generally to catheterization systems, and, more particularly, relates to an apparatus and method for performing central venous catheter insertions and exchanges.

The nutritional and fluid balances of hospital patients can be maintained in part or totally using hyperalimentation (total parenteral nutrition) and parenteral fluid and electrolyte solutions. To implement these techniques, an open-ended catheter is positioned with its distal tip in a large vein of a patient's cardiovascular system. Once the tip is positioned in the target vein, the catheter is used to deliver a highly concentrated nutrient solution. The high volume of blood flowing through the vein rapidly dilutes the nutritional solution, thus decreasing the risk of pain, venous inflammation, or thrombosis. Typically, the catheter is positioned to pass through the subclavian or internal jugular vein into the superior vena cava. The same method may be used for delivery of various drugs which cannot be delivered through peripheral veins.

After extended use, catheters can become clogged, bent, suspected of infection, or otherwise inoperative and must be replaced. Following the prior technique of catheter replacement, a guidewire is inserted into the catheter-to-be-removed, the catheter withdrawn, and a replacement catheter slidingly advanced over the guidewire. Unfortunately, this technique of catheter replacement often results in an undesirable irritation of the heart. This irritation results from overinsertion, or overshoot, of the guidewire and/or replacement catheter close to or into the heart.

Several factors contribute to overinsertion of the guidewire. First, the generous lengths of conventional double and triple lumen catheters (35–43 cm) and the accompanying guidewires (60–68.5 cm) often leads to difficulty in accurately estimating the amount of wire inserted. Second, during catheter manipulation, both in and out over the guidewire, the wire is frequently moved despite the operator's belief that the wire is being held stationary. Further, in clinical situations the combined goals of maintaining venous access, controlling the free end of the wire, preserving sterility, and sometimes calming a tense patient all compete for the operator's attention, making estimation of wire length and catheter manipulation even more difficult. The results of recent research indicate that sustained and dangerous arrhythmias can result from guidewire stimulation. More particularly, about forty-one percent of guidewire-directed catheter exchanges result in a wide range of atrial arrhythmias. Twenty-five percent of these exchange procedures produce ventricular ectopy, of which thirty percent are ventricular couplets or more malignant ventricular arrhythmias. Research indicates that these arrhythmias often resolve spontaneously with the guidewire still in place or shortly after its withdrawal. Occasionally these arrhythmias continue and may become hemodynamically significant. It is clear that avoidance of overinsertion of the catheter/guidewire assembly is desirable.

In order to avoid such overshoot, and the resulting problems, the placement of catheters might be accomplished while radiographic monitoring is used to track the position of the catheter/guidewire assembly. However, this approach requires increased exposure to radiation, as well as significant additional time and expense.

Accordingly, an object of the invention is to provide an improved method and apparatus for accurately positioning catheters within a vein.

A further object of the invention is to provide an apparatus and method which acts to decrease the chances of cardiac irritation during insertion or exchange of central venous catheters.

These and other objects and features of the invention will be apparent from the following description of the preferred embodiments and from the drawings.

SUMMARY OF THE INVENTION

The invention attains the preceding objects and features by providing a method and apparatus for the insertion and replacement of central venous catheters. The basic apparatus includes a substantially translucent catheter and a guidewire having a series of markings thereon over which the catheter is inserted.

The guidewire has sufficient flexibility that it may be slipped along a convoluted passageway, i.e., the inside of a catheter or vein. In order to determine the length of guidewire inserted into a patient's cardiovascular system, and to be able to maintain the guidewire at a substantially constant location, the guidewire has a series of marks on its surface. Preferably, the marks on the guidewire are in the form of a metric scale which can run from either end of the guidewire.

The catheter is formed primarily of a translucent, non-thrombogenic material, or a material with a non-thrombogenic surface coating. The catheter includes a tubular portion which defines at least one lumen extending along a longitudinal axis. The catheter also includes an internal guide channel having a cross-section sized such that the catheter channel may slidingly extend about a guidewire. In one embodiment of the invention, the lumen defines the channel. In other embodiments, a separate rib portion defines the channel. Generally, the catheter-forming material has sufficient stiffness to permit slidable placement over the guidewire. Typically, a radiopaque substance is embedded in the catheter-forming material to allow radiographic visualization of the catheter after insertion or exchange.

The material forming the rib portion can be solid or tubular and preferably has a stiffness greater than the material forming the tubular portion. If a tubular material is used for the rib portion, the rib portion may serve as the channel for the guidewire. The use of a rib portion expands the range of materials useful in forming the tubular portion of the catheter so as to include otherwise inappropriate materials which have low stiffness.

In another aspect, the invention provides a method for the insertion of catheters using a guidewire. The guidewires and catheters used in the insertion method of the invention are preferably those described above. To begin the procedure, a guidewire is slipped through a needle into a target vein; the needle is positioned such that it pierces the skin of a patient and provides access to a blood vessel of their cardiovascular system. Once the guidewire is properly positioned in the blood vessel, the needle is slidably removed from the blood vessel leaving the guidewire in place. Next, a catheter formed of a non-thrombogenic, substantially translucent material is slipped over the guidewire until its distal end is in close proximity to the end of the guidewire in the target vein. In the final step, the guidewire is removed from the blood vessel leaving the catheter properly positioned.

An alternative insertion procedure includes slipping a locating catheter through the needle and positioning it as desired in the patient's cardiovascular system. Next, the guidewire is inserted into the locating catheter until its distal end is in close proximity to that end of the locating catheter positioned in the target vein. The needle and locating catheter are then slidably removed from the blood vessel leaving the guidewire in place. A final catheter is then slipped over the guidewire until its distal end is in close proximity to the distal end of the guidewire. To complete the procedure, the guidewire is removed from the blood vessel leaving the catheter properly positioned. The locating and final catheter can be the same catheter.

Throughout both insertion procedures, the length of guidewire inserted in the blood vessel is maintained substantially constant by, in part, observing the relative position of the marks on the guidewire and the skin of the patient.

The invention also provides a method for the replacement of catheters using a guidewire. The procedure comprises replacing, or exchanging, a first catheter with a second catheter formed of a non-thrombogenic, substantially translucent material. Of course, a material having a non-thrombogenic coating can also be used. Once again, the guidewires and catheters used in the method of the invention are preferably those described above.

To begin the exchange procedure, a guidewire is slid along the lumen (or channel of a rib portion) of the first, already inserted catheter until the distal end of the guidewire is in close proximity to the end of the first catheter. The length of guidewire inserted into the blood vessel is maintained substantially constant by observing, through the translucent sidewall of the first catheter, the relative position of the marks on the guidewire to an aperture in the outer surface of the skin. Having established the preferred position of the guidewire, the first catheter is slid over the guidewire until removed from the blood vessel. During this removal, the guidewire is maintained substantially stationary, in part through the observation of the guidewire marks through the catheter walls.

The second catheter is then slid over the guidewire into the blood vessel while maintaining the guidewire substantially stationary again, in part, through the observation of the guidewire marks. Preferably, the second catheter is inserted into the vein until its end is in close proximity to the end of the guidewire. In the final step of the procedure, the guidewire is removed from the blood vessel by sliding it out through the second catheter, while maintaining the second catheter in place. This procedure maintains the end of the guidewire in a substantially constant location during the exchange so that movement of the guidewire within the blood vessel is decreased and cardiac irritation avoided.

The invention will be more clearly defined in the following description of the drawings and detailed description.

BRIEF DESCRIPTION OF THE DRAWINGS

For a fuller understanding of the nature and objects of the invention, reference should be made to the following detailed description and the accompanying drawings, in which:

FIG. 1A is a perspective view illustrating the same embodiment of FIG. 1 except multiple lumens instead of a single lumen is shown.

FIG. 2A is a perspective view of the same embodiment as FIG. 2 except the rib portion is tubular.

FIGS. 4A-4E are a schematic representation of a central venous catheter replacement procedure, or exchange, in accordance with the invention.

Like reference characters in the respective FIGS. indicate corresponding parts.

DESCRIPTION OF PREFERRED EMBODIMENTS

The present invention provides an apparatus and methods for the insertion and replacement of central venous catheters over a guidewire without causing cardiac arrhythmias. The apparatus includes two parts: a guidewire having markings thereon; and a translucent catheter. The markings on the guidewire are used to maintain the position of the guidewire substantially constant once inserted into a patient's cardiovascular system, and thus avoid over-insertion and related cardiac irritation. As used herein the terms "catheter replacement procedure" and "catheter exchange" are synonymous.

Figure 1:
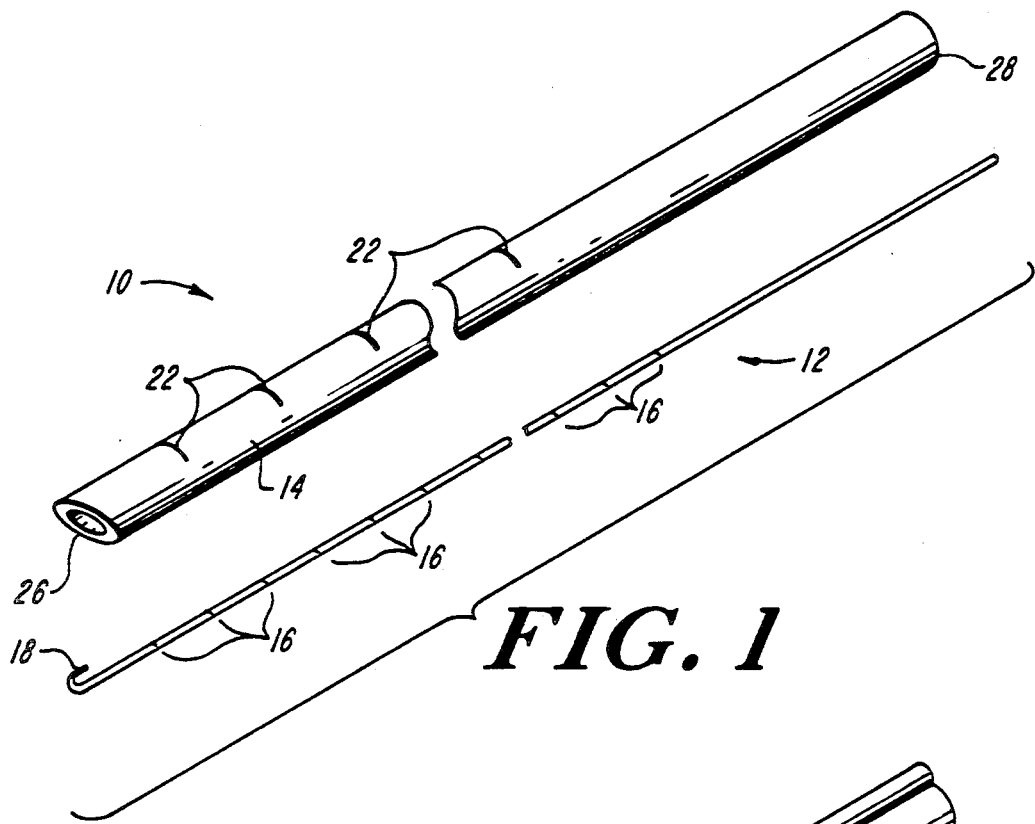
FIG. 1 is a perspective view illustrating a first embodiment of the invention including a catheter having a central lumen, and a guidewire.

FIGS. 1 and 1A depict a central venous catheter system 10 including a flexible guidewire 12 and tubular catheter 14. In the illustrated embodiment, the guidewire 12 has a series of uniformly spaced markings 16 and a substantially J-shaped distal end 18. Of course, the distal end 18 can have any shape which permits guidewire movement without traumatization of the internal wall of the blood vessel. Guidewire 12 is manufactured of any flexible material which has sufficient stiffness to facilitate the insertion or exchange of catheters without becoming jammed. Typically, the guidewire 12 is manufactured from 0.035 inch diameter stainless steel or aluminum wire, or other similar materials. Preferably, the guidewire 12 is about sixty-five to seventy centimeters in length or between fifteen and twenty-five centimeters longer than the catheter 14. The guidewire 12 has markings 16, commencing about twelve to eighteen centimeters from the substantially J-shaped end 18, which are arranged in the form of a metric scale. Markings 16 contrast sufficiently with the color of the guidewire 12 so that they are visible through the catheter 14 during an insertion or exchange procedure.

The catheter 14 has uniformly spaced markings 22 positioned along its length, a distal end 26, and a proximal end 28. Catheter 14 preferably is manufactured from a translucent material, and is typically twenty-four to forty-five centimeters in length with a 0.037 inch inner diameter. A series of uniformly spaced markings 22, in the form of a metric scale, are positioned along the catheter 14. Typically, the markings 22 are at 5 cm, 10 cm and 15 cm from the distal end 26. The distal end 26 of the catheter 14 can be tapered to facilitate insertion and advancement of the catheter 14 in the vein. The catheter can also be embedded with a radiopaque marker 27 at distal end 26 or if a multi-lumen catheter is used, at the side-ports (not shown). In another embodiment, shown in FIG. 2, the catheter 14 can include a relatively stiff rib portion 24.

The catheter 14 can be of single (FIG. 1) or multi-lumen (FIG. 1A) construction and is formed prrmarily of a translucent, non-thrombogenic material. Alternatively, a substrate coated with a non-thrombogenic material can be used. Translucent, as used herein, includes suitable transparent or clear materials. The catheter 14 is translucent over a portion sufficient to permit a physician to see and use the markings 16 as a guide to the relative position of the guidewire 12 in the vein. Further, the catheter-forming material has sufficient stiffness to permit placement over the guidewire 12 and negotiation of a tortuous vascular path. Catheter 14 is of sufficient length to extend from an aperture in the skin of a patient to a vein which will not be adversely affected by intravenous therapy or therapeutic agent administration. Although the actual length of the catheter 14 will depend upon the size of the patient and the intended therapy to be administered, the catheter 14 preferably will be of sufficient length to extend from the superior vena cava to the deltapectoral groove or anterior lateral neck and further to a point midway down the anterior wall of the chest, a distance of about twenty to forty-five centimeters.

Generally, the catheter 14 has a relatively small outside diameter so that it can be readily inserted into a vein without causing extensive trauma to the vein or surrounding tissue. A translucent dilator, ten to fifteen centimeters in length, is particularly useful to introduce the catheter into a patient's blood vessel. In operation, the markings on the guidewire and catheter can be observed through the dilator The inside diameter of the catheter 14 is sufficient to permit an intravenous solution to flow therethrough at a rate sufficient to allow the required amount of nutrients or therapeutic agents to be delivered. In embodiments where the lumen defines a channel for a guidewire, the inside diameter of the catheter 14 must be sufficient to accommodate guidewire 12.

Figure 2:
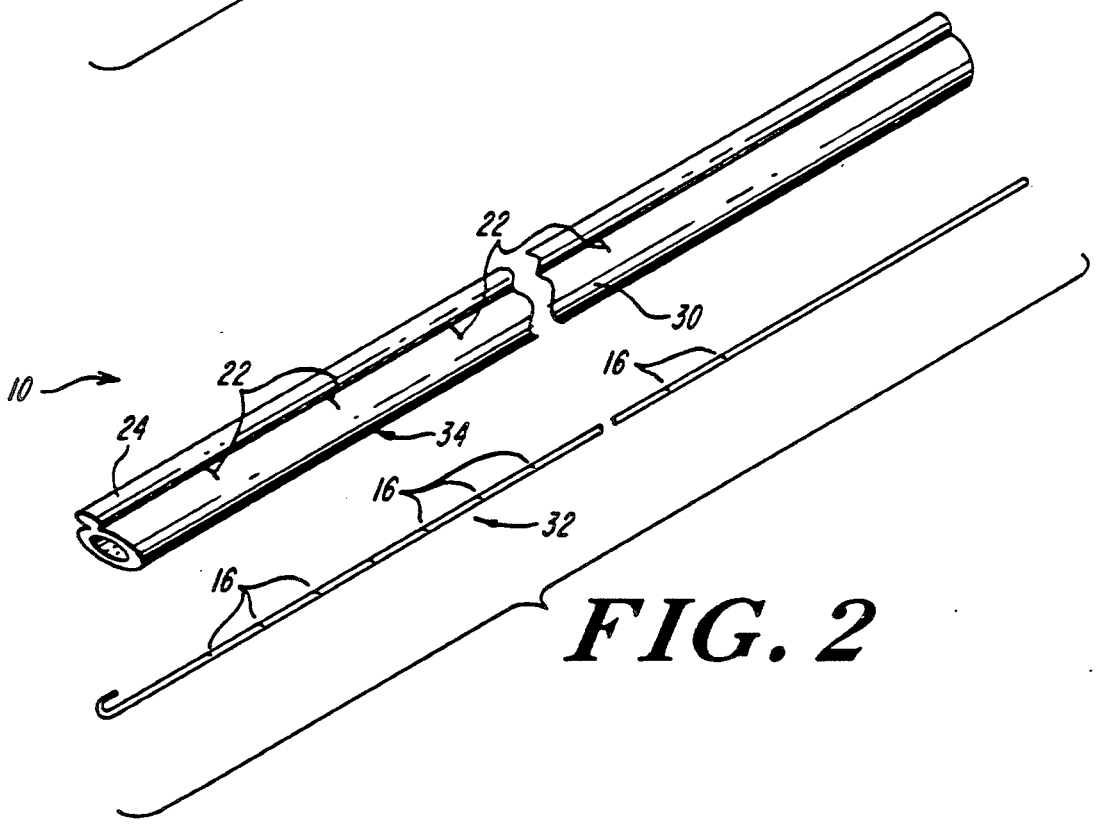
FIG. 2 is a perspective view illustrating a second embodiment of the invention including a catheter having a tubular portion and a rib portion, and a guidewire.

FIGS. 2 and 2A depict an alternative embodiment of the central venous catheter system 10 in which catheter 34 (similar to catheter 14) includes a tubular, lumen-defining portion 30 and a rib portion 24 integral with the tubular portion 30. The rib portion 24 can be of either solid (FIG. 2) or tubular (FIG. 2A) construction and preferably has greater stiffness than the material forming the tubular portion 30. The structural support afforded by the rib portion 24 expands the range of materials to include those with low dimensional stability, e.g., those sold under the registered trademark SILASTIC, that can form the tubular portion 30 of the catheter 34. The composite structure of catheter 34 has a relatively small outside diameter so that it can be readily inserted into a vein without causing extensive trauma, and the lumen of tubular portion 30 has an inside diameter sufficient to permit delivery of the required amount of nutrients or therapeutic agents.

FIGS. 3A through 3F depict in sequence an insertion procedure using the catheterization system 10 of the present invention.

Figure 3A:
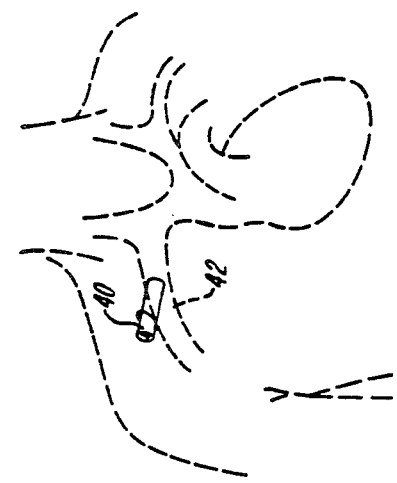
FIGS. 3A-3F are a schematic representation of a central venous catheter insertion procedure in accordance with the invention.
Figure 3B:
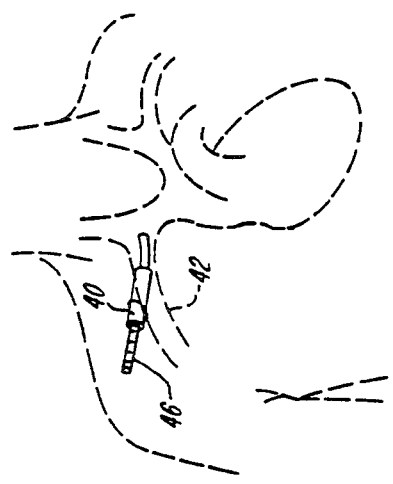
Figure 3C:
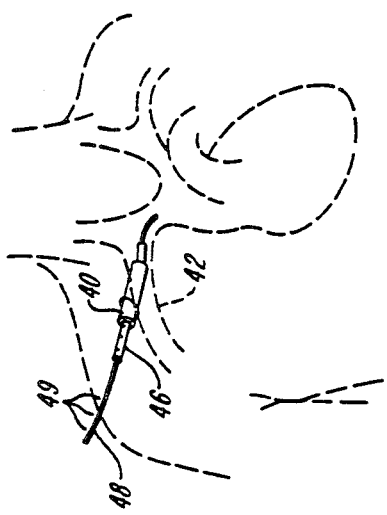
Figure 3D:

The first phase of the method is directed toward the placement of a locating catheter and a guidewire therein. As shown in FIG. 3A, a needle 40 having a bore is inserted through the skin of a patient and into a blood vessel 42. In the next step, depicted in FIG. 3B, the locating catheter 46 is slid through the bore of the needle 40 and, along the blood vessel 42, until its end resides at a predetermined location within the blood vessel 42 (or other vessel which will not be adversely affected by intravenous therapy or therapeutic agent administration). The position of the locating catheter 46 can be determined by using radiographic techniques familiar to those skilled in the art. Next, a flexible guidewire 48 is slid into the locating catheter 46 as indicated in FIG. 3C. The guidewire 48 has marks 49 to indicate its position relative to the skin of the patient and a diameter smaller than the inner diameter of the locating catheter 46. The locating catheter 46 and needle 40 are then sequentially removed from the blood vessel 42 by sliding them over guidewire 48 thus leaving the guidewire 48 positioned in the blood vessel 42 as shown in FIG. 3D. During this removal step, the position of the guidewire 48 is maintained substantially constant by, in part, observing the position of the marks 49 relative to the patient's skin.

Figure 3E:
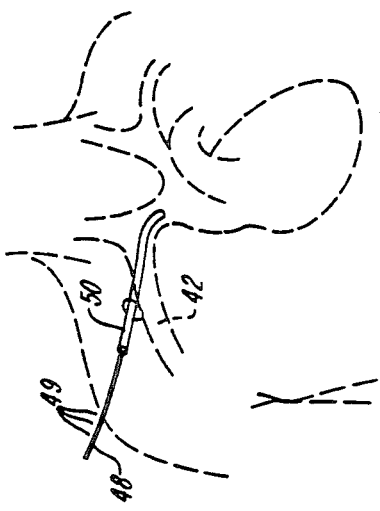

In the next phase of the insertion, depicted in FIG. 3E, a final catheter 50 is slid over the guidewire 48 until its distal end is positioned in close proximity to the distal end of the guidewire 48. Based upon radiographic data, the amount catheter inserted, and hence its final position, may be adjusted as desired using the marks 49 on the guidewire 48 as a guide. The insertion of the catheter 50 is performed while maintaining the guidewire 48 at a substantially constant position by again observing the position of the marks 49 relative to the patient's skin.

Figure 3F:
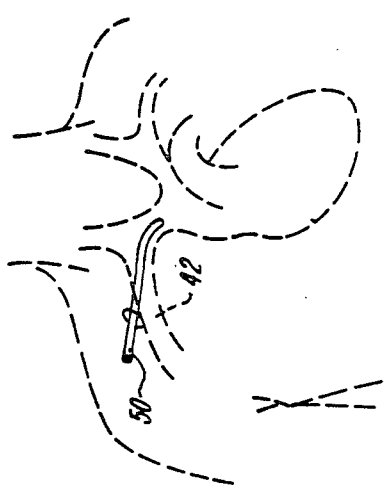

Having positioned the final catheter 50 in the blood vessel 42, the guidewire 48 is removed, while maintaining the position of the catheter 50 substantially constant, thus leaving the catheter 50 positioned therein as indicated in FIG. 3F. The locating catheter 46 and final catheter 50 can be the same catheter.

The insertion procedure of the invention can be also be performed using the guidewire 48 as the initial positioning element. To commence this procedure, the needle 40 is inserted into the patient; guidewire 48 is then inserted through the needle 40 and threaded through the patient's cardiovascular system into the desired blood vessel. Once the guidewire 48 is positioned, the needle 40 is slidably removed over the guidewire 48, as shown in FIG. 3D, while maintaining the position of the guidewire 48 substantially constant by, in part, noting the position of the marks 49 on the guidewire 48 relative to the patient's skin. Following removal of the needle, a dilator can be temporarily slid over the guidewire 48 and partially into the blood vessel of the patient to increase the size of the puncture and thus permit easier insertion of the catheter. The remainder of the procedure, i.e., the insertion of the catheter and removal of the guidewire, is in accordance with the procedure described above with respect to FIGS. 3E and 3F.

The procedures described in connection with FIGS. 3A through 3F permit catheterization of patients in conjunction with the removal of the insertion needle 40. The removal of the needle 40 is preferred since it decreases the risk of infection by permitting the patient's skin to seal around final catheter 50. In most situations, removal of the needle 40 is impossible due to either the extreme length of the guidewire, and the above-discussed problems resulting therefrom, or the presence of a hub on the catheter. Since catheter insertions are performed more often than catheter exchanges, many patients require only one catheter, the use of the catheterization system 10 prevents a greater overall number of complications than observed in conjunction with catheter exchanges.

FIGS. 4A through 4E depict in sequence the replacement procedure using the central venous catheter system 10 of the present invention. As shown in FIG. 4A, patients undergoing hyper-alimentation typically already have a first catheter 51 passing through an aperture 52 in the skin of a patient, with the distal end of catheter 51 being positioned in the superior vena cava 53. The pre-exchange position of the first catheter 51 can be determined using radiography procedures and equipment familiar to those skilled in the art.

In the first step of the replacement procedure, shown in FIG. 4B, the user slides a guidewire 54 into the first catheter 51 until the end of guidewire 54 reaches the end of first catheter 51 positioned within vein 53. The physician then notes the position of the markings 58 on the guidewire 54 with respect to the aperture 52 so as to establish the relative position of the guidewire 54 in the cardiovascular system.

The next step, indicated in FIG. 4C, includes removing the first catheter 51 from the vein while maintaining the guidewire 54 at a substantially constant position, using the markings 58 to determine the guidewire's position. During this step, the position of guidewire 54 is determined by monitoring the markings 58 through the translucent sidewalls of catheter 51. By maintaining the guidewire 54 in a generally constant position, and out of contact with the heart wall, the insertion of additional guidewire into or near the right atrium or ventricle of the heart is avoided and the occurrence of arrhythmias is greatly reduced.

Once the first catheter 51 is removed, the user slides a second (replacement) catheter 56 over the guidewire 54 until that catheter is positioned with its distal end in close proximity to the end of guidewire 54 in the superior vena cava 53 (FIG. 4D). Once again, the relative position of the markings 58 on the guidewire 54 with respect to the aperture 52 in the outer surface of the skin are noted, and maintained constant, so that the length of guidewire 54 inserted into the superior vena cava 53 remains substantially constant. The second catheter 56 is typically inserted until it contacts the substantially J-shaped end of the guidewire 54.

In the final step of the procedure, indicated in FIG. 4E, the guidewire 54 is removed from the vein, leaving the second catheter 56 at a location substantially identical to that occupied by the first catheter 51.

Since the guidewire 54 acts to guide the second catheter 56 to a location substantially identical to that occupied by the first catheter 51, extensive radiography to track the progress of the catheter insertion, and confirm its final position, is unnecessary. Accordingly, the apparatus and method of the invention advantageously provides a means for lowering the amount of radiation exposure, i.e., x-ray exposure, for patients undergoing exchange procedures and the overall cost of the procedure.

It will be understood that although the above description details a process for central venous catheterization, the apparatus and methods of the invention can also be employed in other components of the cardiovascular system, e.g., the pulmonary vascular system.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for the placement of a catheter into a blood vessel comprising the steps of:
   A. inserting a needle having a bore through the skin of a patient and into said blood vessel such that a first portion of said needle resides within said blood vessel and a second portion outside said blood vessel;
   B. sliding a guidewire through said bore of said needle and along said blood vessel until a first end of said guidewire resides at a predetermined location within said blood vessel and a second end resides outside said blood vessel, said guidewire having a diameter smaller than an inner diameter of said catheter and said guidewire also having marks thereon for indicating the position of said guidewire relative to the skin of said patient;
   C. removing said needle from said blood vessel by sliding said needle over said guidewire while maintaining said guidewire at a substantially constant position by observing the position of said marks relative to the skin of said patient;
   D. sliding said catheter over said guidewire until the distal end of said catheter is positioned in close proximity to the distal end of said guidewire while maintaining said guidewire at a substantially constant position by observing the position of said marks relative to the skin of said patient, said catheter having a tubular portion defining at least one central lumen, said catheter being formed of a translucent material, and said catheter including an internal channel extending along said axis, said channel having a cross-section sized such that said catheter is slidable over said guidewire; and
   E. removing said guidewire while maintaining said catheter in place in said blood vessel.

2. The method of claim 1 wherein said catheter comprises a plurality of lumens.

3. The method of claim 1 wherein said tubular portion of said catheter comprises a plurality of lumens.

4. A method for the replacement of a first catheter having a first end residing within a blood vessel and a second end outside said blood vessel with a second catheter, said first catheter extending through an aperture in the skin of a patient, said first and second catheters each having a tubular portion defining at least one central lumen, said second catheter being formed of a translucent material, said catheters each including an internal channel, said channels having cross-sections sized such that said catheters are slidable over a guidewire, comprising the steps of:
   A. sliding a flexible guidewire having a distal end and a proximal end into said channel of said first catheter until the distal end of said guidewire is positioned in the first end of said first catheter, said guidewire having marks thereon for indicating the position of said guidewire relative to said aperture;
   B. removing said first catheter from said blood vessel by sliding said first catheter over said guidewire while maintaining said guidewire at a substantially constant position by observing the position of said marks relative to said aperture;
   C. sliding said second catheter over said guidewire until the distal end of said second catheter is in close proximity to said distal end of said guidewire while maintaining said guidewire at said substantially constant position by observing through said second translucent catheter the position of said marks relative to said aperture; and D. removing said guidewire while maintaining said second catheter in place in said blood vessel.

5. The method of claim 4 wherein said second catheter further comprises a stiffening rib portion formed of a material which has greater stiffness than the material forming said tubular position.

6. The method of claim 5 wherein said rib portion comprises a solid material, and wherein one of said lumens defines said channel.

7. The method of claim 5 wherein said rib portion comprises a tubular material defining said channel.

8. The method of claim 4 wherein said tubular portion of the second catheter comprises a plurality of lumens.

9. A method for the placement of a catheter into a blood vessel comprising the steps of:

A. inserting a needle having a bore through the skin of a patient and into said blood vessel such that a first portion of said needle resides within said blood vessel and a second portion outside said blood vessel;

B. sliding a locating catheter through said bore of said needle to a predetermined location in said blood vessel, said locating catheter having a tubular portion defining at least one central lumen, said locating catheter being formed of a translucent material and including an internal channel;

C. sliding a guidewire through said bore of said needle and along said blood vessel until a first end of said guidewire resides at a predetermined location within said blood vessel and a second end resides outside said blood vessel, said guidewire having a diameter smaller than an inner diameter of said catheter and said guidewire also having marks thereon for indicating the position of said guidewire relative to the skin of said patient;

D. removing said needle from said blood vessel by sliding said needle over said guidewire while maintaining said guidewire at a substantially constant position by observing the position of said marks relative to the skin of said patient;

E. sliding said catheter over said guidewire until the distal end of said catheter is positioned in close proximity to the distal end of said guidewire while maintaining said guidewire at a substantially constant position by observing the position of said marks relative to the skin of said patient, said catheter having a tubular portion defining at least one central lumen, said catheter being formed of a translucent material, and said catheter including an internal channel extending along said axis, said channel having a cross-section sized such that said catheter is slidable over said guidewire; and F. removing said guidewire while maintaining said catheter in place in said blood vessel.

10. The method of claim 9 wherein said step of sliding said guidewire through said bore of said needle includes sliding said guidewire through said channel of said locating catheter until the distal end of said guidewire is positioned in close proximity to the end of said locating catheter residing at said predetermined location in said blood vessel.

11. The method of claim 10 further comprising the step of removing said locating catheter from said blood vessel after insertion of said guidewire by sliding said locating catheter over said guidewire while maintaining said guidewire at a substantially constant position by observing the position of said marks on said guidewire relative to the skin of said patient.

12. The method of claim 11 wherein said locating catheter and said finally introduced catheter are the same catheter.

13. A method for the placement of a catheter into a blood vessel comprising the steps of:

A. inserting a needle having a bore through the skin of a patient and into said blood vessel such that a first portion of said needle resides within said blood vessel and a second portion outside said blood vessel;

B. sliding a guidewire through said bore of said needle and along said blood vessel until a first end of said guidewire resides at a predetermined location within said blood vessel and a second end resides outside said blood vessel, said guidewire having a diameter smaller than an inner diameter of said catheter and said guidewire also having marks thereon for indicating the position of said guidewire relative to the skin of said patient;

C. removing said needle from said blood vessel by sliding said needle over said guidewire while maintaining said guidewire at a substantially constant position by observing the position of said marks relative to the skin of said patient;

D. sliding said catheter over said guidewire until the distal end of said catheter is positioned in close proximity to the distal end of said guidewire while maintaining said guidewire at a substantially constant position by observing the position of said marks relative to the skin of said patient, said catheter having a tubular portion defining at least one central lumen, said catheter being formed of a translucent material, and said catheter including a stiffening rib portion formed of a material which has greater stiffness than the material forming said tubular portion and an internal channel extending along said axis, said channel having a cross-section sized such that said catheter is slidable over said guidewire; and E. removing said guidewire while maintaining said catheter in place in said blood vessel.

14. The method of claim 13 wherein said rib portion comprises a solid material, and wherein one of said lumens defines said channel.

15. The method of claim 13 wherein said rib portion comprises a tubular material defining said channel.

* * * * *